United States Patent [19]

Mahurkar

[11] Patent Number: 4,808,155
[45] Date of Patent: Feb. 28, 1989

[54] SIMPLE DOUBLE LUMEN CATHETER

[76] Inventor: Sakharam D. Mahurkar, 6171 N. Sheridan Rd.-#1112, Chicago, Ill. 60660

[21] Appl. No.: 97,378

[22] Filed: Sep. 16, 1987

Related U.S. Application Data

[63] Continuation of Ser. No. 833,978, Feb. 27, 1986, abandoned, which is a continuation of Ser. No. 544,883, Oct. 24, 1983, abandoned.

[51] Int. Cl.$^4$ ............................................. A61M 25/00
[52] U.S. Cl. ......................................... 604/43; 604/4; 604/280
[58] Field of Search ........................... 604/4, 5, 43–45, 604/280–284

[56] References Cited

U.S. PATENT DOCUMENTS

| | | | |
|---|---|---|---|
| D. 250,349 | 11/1978 | McFarlane | D24/54 |
| D. 254,444 | 3/1980 | Levine | D24/54 |
| 256,590 | 4/1882 | Pfarre | 604/43 |
| D. 256,617 | 8/1980 | Clemens | D24/54 |
| D. 272,651 | 2/1984 | Mahurkar | 604/44 X |
| 701,075 | 5/1902 | McCully | 604/43 |
| 998,339 | 7/1911 | Hollins | 27/24 A |
| 1,045,326 | 11/1912 | Ruflin | 604/43 |
| 1,093,538 | 4/1914 | Clough | 128/343 |
| 1,290,647 | 1/1919 | Nyvall | 128/214 R X |
| 1,922,084 | 8/1933 | Gerow | 128/349 |
| 2,175,726 | 10/1939 | Gebauer | 128/349 B |
| 2,230,218 | 2/1941 | Asche | 128/276 |
| 2,409,343 | 10/1946 | Curtis | 128/214 |
| 2,473,742 | 6/1949 | Auzin | 128/349 |
| 2,474,665 | 6/1949 | Guarino | 128/DIG. 3 |
| 2,564,977 | 8/1951 | Hsi Hu | 128/221 X |
| 2,590,895 | 4/1952 | Scarpellino | 128/221 |
| 2,625,932 | 1/1953 | Salisbury | 128/214.2 |
| 2,716,983 | 9/1955 | Windischman et al. | 128/221 |
| 2,819,718 | 1/1958 | Goldman | 128/350 |
| 2,930,378 | 3/1960 | Buyers | 128/354 |
| 3,042,045 | 7/1962 | Sheridan | 128/349 |
| 3,175,554 | 3/1965 | Stewart | 128/2 |
| 3,314,430 | 4/1967 | Alley et al. | 128/350 |
| 3,324,853 | 6/1967 | Czorny et al. | 128/214.4 |
| 3,331,371 | 7/1967 | Rocchi et al. | 128/349 |
| 3,359,974 | 12/1967 | Khalil | 128/2.05 |
| 3,394,705 | 7/1968 | Abramson | 128/349 |
| 3,435,826 | 1/1969 | Fogarty | 128/348 |
| 3,437,088 | 4/1969 | Bielinski | 128/2 |
| 3,448,739 | 6/1969 | Stark et al. | 128/2.05 |
| 3,452,756 | 7/1969 | Harautuneian | 128/349 |
| 3,463,152 | 8/1969 | Sorenson | 128/214.4 |
| 3,467,101 | 9/1969 | Fogarty et al. | 128/348 |
| 3,543,758 | 12/1970 | McWhorter | 128/349 |
| 3,543,759 | 12/1970 | McWhorter | 128/349 |
| 3,550,591 | 12/1970 | MacGregor | 128/214.4 |
| 3,566,874 | 3/1971 | Sheperd et al. | 128/349 |
| 3,593,713 | 7/1971 | Bogoff et al. | 128/246 |
| 3,599,620 | 8/1971 | Balin | 128/349 B |
| 3,634,924 | 1/1972 | Blake et al. | 29/447 |
| 3,683,908 | 8/1972 | Michael et al. | 128/145.7 |
| 3,726,281 | 4/1973 | Norton et al. | 128/349 R |

(List continued on next page.)

FOREIGN PATENT DOCUMENTS 834211 2/1976 Belgium ............................. 128/221

(List continued on next page.)

OTHER PUBLICATIONS

McIntosh et al., "Double Lumen Catheter," *J.A.M.A.*, Feb. 21, 1959, pp. 137/835-138/836.

(List continued on next page.)

*Primary Examiner*—Dalton L. Truluck
*Attorney, Agent, or Firm*—Stephen G. Rudisill

[57] ABSTRACT

A double lumen catheter having an elongated tube with a proximal cylindrical portion enclosing first and second lumens separated by an internal divider, the proximal end of the elongated tube connecting to two separate connecting tubes communicating with the respective first and second lumens for the injection and removal of blood, the first lumen extending from the proximal end of the elongated tube to a first opening at the distal end of the elongated tube, and the second lumen extending from the proximal end of the elongated tube to a second opening spaced a sufficient distance away from the first opening, in the longitudinal direction, to prevent mixing of the returned blood with the blood taken in, the tube having a non-conical and non-tapered distal end portion having a reduced cross-sectional area and extending from said second opening and terminating in a blunt end to prevent the end of the catheter from traumatizing or becoming caught in the walls of a blood vessel into which the catheter is inserted.

12 Claims, 1 Drawing Sheet

U.S. PATENT DOCUMENTS

| | | |
|---|---|---|
| 3,746,003 | 7/1973 | Blake et al. ............... 128/349 B |
| 3,756,234 | 9/1973 | Kopp ............................ 128/214 R |
| 3,771,527 | 11/1973 | Ruisi ............................ 128/350 R |
| 3,774,605 | 11/1973 | Jewett .......................... 128/214.4 |
| 3,799,172 | 3/1974 | Szpur ........................... 128/349 R |
| 3,804,097 | 4/1974 | Rudie ........................... 128/350 R |
| 3,823,720 | 7/1974 | Tribble ......................... 128/350 R |
| 3,828,767 | 8/1974 | Spiroff ......................... 128/2.05 |
| 3,830,234 | 8/1974 | Kopp ............................ 128/214 R |
| 3,875,938 | 4/1975 | Mellor .......................... 128/214.4 |
| 3,885,567 | 5/1975 | Ross ............................. 128/278 |
| 3,896,815 | 7/1975 | Fettel et al. ................. 128/348 |
| 3,978,863 | 9/1976 | Fettel et al. ................. 128/348 |
| 4,004,588 | 1/1977 | Alexander ................... 128/241 |
| 4,016,879 | 4/1977 | Mellor .......................... 128/214.4 |
| 4,027,668 | 6/1977 | Dunn ........................... 128/214 R |
| 4,037,599 | 7/1977 | Raulerson ................... 128/214.4 |
| 4,057,065 | 11/1977 | Thow ........................... 128/348 |
| 4,072,146 | 2/1978 | Howes ......................... 128/2.05 D |
| 4,096,860 | 6/1978 | McLaughlin ................ 128/214.4 |
| 4,098,275 | 7/1978 | Consalvo .................... 128/221 X |
| 4,099,528 | 7/1978 | Sorenson et al. .......... 128/214.4 |
| 4,100,246 | 7/1978 | Frisch .......................... 264/230 |
| 4,116,068 | 9/1978 | Megahed .................... 73/425.4 P |
| 4,134,402 | 1/1979 | Marhurhar ................. 604/44 |
| 4,144,884 | 3/1979 | Tersteegen et al. ....... 128/214.4 |
| 4,168,703 | 9/1979 | Kenigsberg ................. 128/748 |
| 4,180,068 | 12/1979 | Jacobsen et al. .......... 128/214 R |
| 4,202,332 | 5/1980 | Tersteegen et al. ....... 128/221 X |
| 4,203,436 | 5/1980 | Grimsrud ................... 128/214 R |
| 4,217,895 | 8/1980 | Sagae et al. ................ 128/214.4 |
| 4,270,535 | 7/1981 | Bogue et al. ............... 128/214.4 |
| 4,314,555 | 2/1982 | Sagae .......................... 128/214.4 |
| 4,336,036 | 6/1982 | Leeke et al. ................ 128/214 R X |
| 4,385,631 | 5/1983 | Uthmann .................... 604/43 X |
| 4,403,983 | 3/1983 | Edelman et al. ........... 604/43 |
| 4,403,985 | 9/1983 | Boretos ....................... 604/53 |
| 4,406,656 | 9/1983 | Hattler et al. .............. 604/280 |
| 4,419,095 | 12/1983 | Nerbergall et al. ........ 604/96 |
| 4,451,252 | 5/1984 | Martin ......................... 604/43 |
| 4,484,585 | 11/1984 | Baier ............................ 128/748 |
| 4,493,696 | 5/1985 | Uldall .......................... 604/43 |
| 4,543,087 | 9/1985 | Sommercorn et al. .... 604/43 |
| 4,568,329 | 2/1986 | Mahurkar ................... 604/43 |
| 4,583,968 | 4/1986 | Mahurkar ................... 604/43 |
| 4,623,327 | 11/1986 | Mahurkar ................... 604/4 |
| 4,643,711 | 2/1987 | Bates ........................... 604/43 X |

FOREIGN PATENT DOCUMENTS

| | | |
|---|---|---|
| 1092927 | 1/1981 | Canada . |
| 50089 | 8/1982 | Canada . |
| 1150122 | 7/1983 | Canada . |
| 1167727 | 5/1984 | Canada . |
| 36642 | 9/1981 | European Pat. Off. . |
| 0079719 | 11/1982 | European Pat. Off. . |
| 935625 | 11/1955 | Fed. Rep. of Germany . |
| 2259865 | 6/1974 | Fed. Rep. of Germany ...... 128/221 |
| 19346 | 6/1982 | Fed. Rep. of Germany . |
| 592193 | 4/1925 | France ........................... 128/214.2 |
| 1285953 | 7/1962 | France . |
| 1508959 | 1/1968 | France . |
| 2285148 | 4/1976 | France . |
| 2297640 | 8/1976 | France . |
| 821344 | 4/1982 | France . |
| 55-88771 | 7/1980 | Japan ............................. 128/348 |
| 1017315 | 5/1983 | U.S.S.R. . |
| 688450 | 3/1952 | United Kingdom . |
| 1419702 | 12/1975 | United Kingdom ............. 128/221 |
| 1006219 | 3/1983 | United Kingdom . |

OTHER PUBLICATIONS

*Dorland's Illustrated Medical Dictionary*, 25th Ed., W. B. Saunders Co., Phila., 1974, p. 274.

Brenner & Rector, *The Kidney*, vol. III, W. B. Saunders Co., Phila., 1976, p. 164.

*ASAIO Abstracts*, vol. 5, 22nd Annual Meeting, San Francisco, California, Apr. 1-3, 1976, p. 52.

Tohuko, J., "Single Two-Lumen Cannula Dialysis", Aug. 1974.

Tsuchida et al., "Single Two-Lumen Cannula Dialysis", Toboku Journal Exp. Med., 1974, pp. 114, 159-101.

Tsuchida et al., "Design of a Two-Lumen-Piercing Needle That is Capable of Carrying Out Dialysis by Single Puncture", Journal of the Urological Society of Japan, vol. 65 (12), 1974, pp. 805-807.

Kaplan et al., "A Co-Axial Dual Flow Catheter/Canula for Single Puncture Dialysis", Dialysis & Transplantation, Dec./Jan. 1977, pp. 38-40, 42, 84.

SIMPLE DOUBLE LUMEN CATHETER

RELATED APPLICATIONS

This is a continuation of co-pending application Ser. No. 833,978, filed on 2/27/86 which is a continuation of Ser. No. 544,883, filed 10/24/83, both now abandoned.

BACKGROUND OF THE INVENTION

1. Field of Invention

The present invention relates to surgical instruments for withdrawing fluids from or introducing fluids into a cavity of the body.

2. Description of the Related Art

As is well known, a catheter is a tubular, flexible, surgical instrument for withdrawing fluids from (or introducing fluids into) a cavity of the body. A double-current catheter is a catheter having two channels; one for injection and one for removal of fluid. *Dorlan's Illustrated Medical Dictionary, Twenty Fifth-Edition* (W. B. Saunders, Philadelphia 1974), p. 274. As is well known, a double-current catheter is used for removing blood from a fistula or vein for processing in a dialysis machine and returning the processed blood back to the fistula or vein. A double-current catheter suitable for this purpose is disclosed in Mahurkar, U.S. Pat. No. 4,134,402 issued Jan. 16. 1979. Mahurkar U.S. Pat. No. 4,134,402 discloses a double lumen continuous flow hemodialysis needle and cannula having contiguous lumens of different lengths formed by dividing a unitary straight tube, the shorter lumen acting as a blood intake lumen and the longer acting as a blood return lumen. A sharp penetrating bevel is provided on the distal tip for percutaneous entry into a fistula. Semi-circular lumens provide a minimal resistance to blood flow resulting in a smaller but highly efficient catheter in comparison to a coaxial double-current catheter. Hemodialysis requires, for example, a blood flow rate of about 200ml/min or more and flow resistance less than about 100 mm of mercury.

There are numerous other United States Patents disclosing double-current catheters for hemodialysis and evidencing a long-felt need for a small, functionally efficient catheter having a minimum of insertion trauma and potential for clotting. McLaughlin, U.S. Pat. No. 4,096,860 issued June 27, 1978 discloses a coaxial hemodialysis catheter said to allow a step enlargement of the opening of a blood vessel to avoid tearing and rupture of the side walls. A simultaneous flow device incorporates a hub with an extension conduit and a valve therein for receipt of a needle therethrough. The extension conduit is of sufficient size to allow the passage of the needle therethrough adjacent the interior side walls thereof with an attendant extension thereof from its opening. The needle with the extension conduit is adapted for combined insertion within a blood vessel, after which it can be withdrawn while the valve prevents the backflow of blood through the axial passage of the hub. A coaxial flow device can then be inserted within the hub conduit.

Sorensen et al., U.S. Pat. No. 4,099,528 issued July 11, 1978 discloses a coaxial double lumen cannula mounted upon a hub and having a central stylet needle for penetrating a patient's vein and which is retractable after penetration.

Grimsrud, U.S. Pat. No. 4,203,436 issued May 20, 1980 discloses a hollow hypodermic needle with a divider for providing a first channel for removal of blood for treatment from a punctured blood vessel and a second channel for returning the treated blood to the blood vessel.

Uthmann, U.S. Pat. No. 4,385,631 issued May 31, 1983 discloses a hemodialysis catheter for puncturing blood vessels which includes a section insertable through a puncture opening into a blood vessel and a hose line following thereafter. This catheter has two circular lumens arranged side by side. One of the circular lumens has a sloping bevel while the other circular lumen passes slidably through a sheath integral with the first lumen. This device requires a large puncture opening and produces an inefficient relationship of flow rate to puncture area.

Jacobson et al., U.S. Pat. No. 4,180,068 issued Dec. 25, 1979 discloses a double-current hemodialysis catheter comprising a primary tube and an internal divider which also functions as a trocar and valve. The primary tube has a side opening for receiving blood and a central opening at the distal end of the primary tube. The internal divider includes a cutting end which protrudes from the distal opening when the divider is longitudinally moved to an insert position. In the insert postion, blood flow is blocked.

Mahurkar, U.S. Pat. No. Des. 272,651 issued Feb. 14, 1984 discloses a double lumen catheter having an outlet lumen which has an opening at the tip of the catheter and a shorter inlet lumen which terminates in a bevel substantially displaced from the tip.

Uldall U.S. Pat. No. 272,651 issued Feb. 14, 1984 discloses a double lumen catheter having an outlet lumen which has an opening at the tip of the catheter and a shorter inlet lumen which terminates in a bevel substantially displaced from the tip.

Uldall U.S. Pat. No. 4,493,696 issued Jan. 15, 1985 described a coaxial double lumen catheter in which the outer lumen is constricted at its distal end, and the tip of the inner lumen rests against the beginning of this constriction. Blood is withdrawn for processing through the outer lumen via multiple openings in the outer wall; the processed blood is returned through the inner lumen.

SUMMARY OF THE INVENTION

The primary object of the invention is to provide a simple and efficient double lumen catheter of small size which will not traumatize or become caught in the walls of a blood vessel into which the catheter is inserted, and yet is relatively easy to insert into the blood vessel.

A further object of this invention is to provide a double lumen catheter which is easy and inexpensive to manufacture.

Other objects and advantages of the invention will become apparent from the following detailed description and the accompanying drawings.

While the invention will be described in connection with a certain preferrred embodiment, it will be understood that it is not intended to limit the invention to that particular embodiment. On the contrary, it is intended to cover all alternatives, modifications, and equivalents as may be included within the spirit and scope of the invention as defined by the appended claims.

DETAILED DESCRIPTION OF PREFERRED EMBODIMENTS

Turning now to the drawings, FIGS. 1, 2, 3 and 6 show various external views of a simple double lumen catheter, generally designated 10, in accordance with the present invention. As is conventional for a catheter, the double lumen catheter 10 has an elongated unitary hollow tube 11 which is inserted into a body cavity such as a vein. The major portion of the tube 11 is circular in cross section, as shown in FIG. 5, and has an internal planar axial divider or septum 12 defining a return lumen 13 and an inlet lumen 14 within the interior of the hollow tube 11. This divider 12 is preferably of unitary or one-piece construction with the tube 11, bisecting the tube into the two lumens 13 and 14. The transverse cross-sections of the lumens 13 and 14 are semicircular or "D" shaped (see FIG. 5) which minimizes resistance to fluid flow.

As is conventional for this type of dual lumen construction, the divider 12 extends axially along the interior of the tube 11 from a branching connector 15. The branching connector 15 connects the proximal ends of the return lumen 13 and the inlet lumen 14 to respective fluid return and inlet lines 16 and 17 which are, for example, respective venous and arterial lines of a dialysis or plasmapheresis circuit. The preferred direction of fluid circulation is indicated by dashed arrows in FIG. 1.

The hollow tube 11 includes openings or apertures at the distal end portions of the lumens 13 and 14 to permit the flow of the fluid between a body cavity (not shown) and the lumens. The return lumen 13 extends along the entire length of the tube 11 to an aperture or opening 18 at the distal end of the tube 11 as is more clearly shown in FIG. 4. The inlet lumen 14 is shorter than the return lumen 13 and terminates at an aperture or opening 19 that is substantially displaced from the return aperture 18 at the distal end of the tube 11. Both lumens 13 and 14 are straight along their entire lengths, and thus their respective openings 18 and 19 are aligned with the axes of the respective lumens, but eccentric with respect to the central axis of the tube 11. The longitudinal spacing of the distal openings 18 and 19 prevents mixing of the returned blood with the blood taken in.

In accordance with the invention, the tube 11 terminates with a blunt distal end 20 which is normal to the axis of the catheter 10. It does not have the conical tip or taper that is characteristic of other catheters. The absence of the conical tip avoids trauma and migration of the catheter into the tributaries of the veins, e.g., the blunt end prevents the end of the catheter from traumatizing or becoming caught in the walls of a blood vessel into which the catheter is inserted. The intake lumen 14, on the other hand, preferably forms a bevel 21 at its distal end. Beyond the bevel 21 the divider 12 and half of the hollow tube 11 continue to the blunt distal end portion 20 of the return lumen 13.

Figure 1:
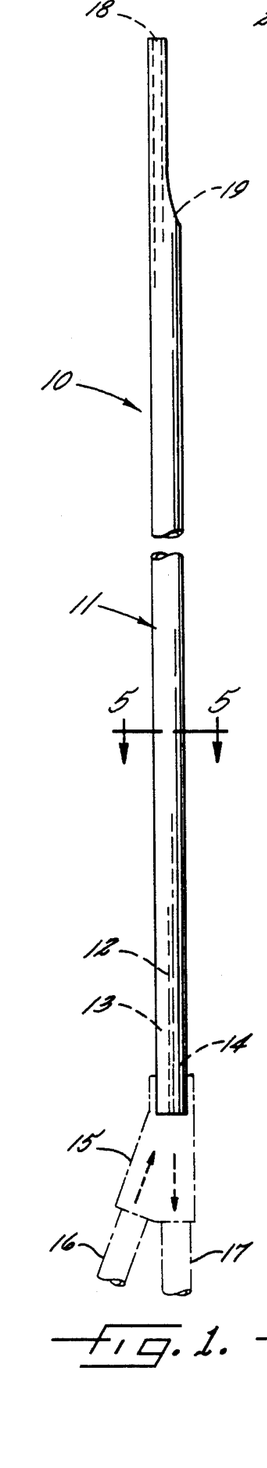
FIG. 1 is a front and rear elevational view of a double lumen catheter embodying my invention.
Figures 2, 3, 4, 5, 6:
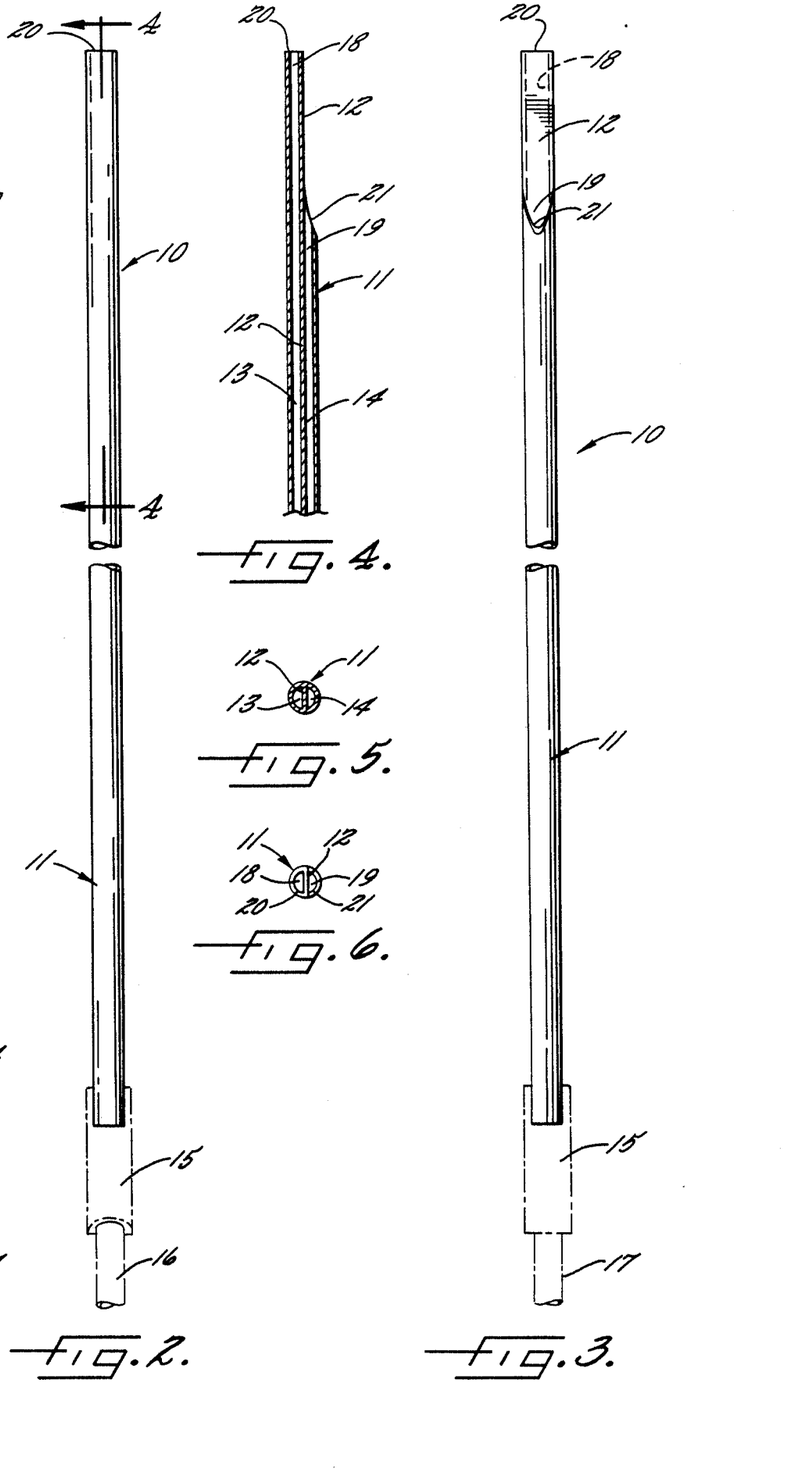
FIG. 2 is a right side elevational view of the catheter illustrated in FIG. 1.
FIG. 3 is a left side elevational view of catheter illustrated in FIG. 1.
FIG. 4 is a section taken generally along line 4—4 thereof in FIG. 2.
FIG. 5 is a section taken generally along line 5—5 in FIG. 1.
FIG. 6 is a top view of the catheter illustrated in FIG. 1.

The dual lumen tube 11 can be formed by extrusion or molding of a polymeric material. After the tube has been cut to the desired length, the bevel 21 is formed by simply cutting the desired angle of bevel through the wall of that half of the tube that forms the lumen 14 (see FIGS. 3 and 4), and then continuing the cut longitudinally along one side of the divider 12 to the distal end of the tube. After this cut portion of the tube has been removed, the divider 12 merges with only about one-half of the cylindrical portion of the tube between the openings 18 and 19, as can be seen in FIGS. 3, 4, and 6.

For use in hemodialysis, the double lumen catheter 10 is introduced in the direction of blood flow in a large vein, surgically under direct vision or over a Seldinger's guide wire through a sheath as is conventional. The inlet opening 19 on the blood inlet lumen 14 draws the blood for processing and the processed blood is returned through the return lumen 13 and out through the hole to return the blood upstream into circulation.

What is claimed is:

1. A double lumen catheter having an elongated tube with a proximal cylindrical portion enclosing first and second lumens separated by an internal divider, the proximal end of said elongated tube connecting to two separate connecting tubes communicating with the respective first and second lumens, the first lumen extending from the proximal end of said elongated tube to a first opening at the distal end of said elongated tube, and the second lumen extending from the proximal end of said elongated tube to a second opening spaced in the longitudinal direction away from said first opening, said tube having a non-conical and non-tapered distal end portion having a cross-sectional area smaller than the cross-sectional area of said proximal cylindrical portion, and said distal end portion extending from said second opening and terminating in a blunt distal end to prevent the distal end of the catheter from traumatizing or becoming caught in the walls of a vessel into which the catheter is inserted.

2. The double lumen catheter as claimed in claim 1, wherein said divider is planar in said cylindrical portion and extends to said blunt distal end to comprise approximately one-half of the peripheral wall of said distal end portion between said first and second openings.

3. The double lumen catheter as claimed in claim 2, wherein said second opening is defined by a bevel arising at its proximal end on the outer periphery of said cylindrical portion opposite the second lumen and terminating at its distal end on the planar divider.

4. The double lumen catheter as claimed in claim 1, wherein the lumens are 'D' shaped in cross-section.

5. The double lumen catheter as claimed in claim 1, wherein
said divider in said cylindrical portion is planar, and each of said lumens is "D" shaped in cross-section along its entire length.

6. The double lumen catheter as claimed in claim 5 wherein said second opening is defined by a bevel arising at its distal end on the outer periphery of said cylindrical portion, and terminating towards the planal divider.

7. A double lumen catheter comprising an elongated unitary tube having a proximal cylindrical portion including a longitudinal septum of one-piece construction with said tube, said septum being planar in said proximal cylindrical portion and dividing the interior of said proximal cylindrical portion into first and second lumens, the proximal end of said tube connecting to two separate tubes communicating with the respective first and second lumens for the injection and removal of fluid, the first lumen extending from the proximal end of said tube to a first opening at the distal end of said tube and the second lumen extending from the proximal end of said tube to a second opening at the distal end of said proximal cylindrical portion, said second opening being spaced in the longitudinal direction away from said first opening, said tube having a distal end portion of substantially uniform cross-section and a cross-sectional area smaller than the cross-sectional area of said proximal cylindrical portion, said distal end portion extending from said second opening and terminating in a blunt end to prevent the end of the catheter from traumatizing or becoming caught in the walls of a vessel into which the catheter is inserted, wherein said septum extends to said blunt distal end to comprise a portion of the peripheral wall of said distal end portion between said first and second openings.

8. The double lumen catheter as claimed in claim 7, wherein the first and second lumens and said distal end portion are each "D" shaped in cross section.

9. A double lumen catheter as claimed in claim 7, wherein said first opening at the distal end of said tube is eccentric with respect to the axis of the cylindrical portion of said tube.

10. A double lumen catheter comprising an elongated tube having a proximal cylindrical portion including a planar axial divider bisecting said cylindrical portion of the tube into first and second lumens, the proximal end of said tube connecting two separate tubes communicating with the respective first and second lumens for the injection and removal of fluid, the first lumen extending from the proximal end of said tube to a first opening at the distal end of said tube, the second lumen extending from the proximal end of said tube to a second opening at the distal end of said proximal cylindrical portion, said second opening being spaced in the longitudinal direction away from said first opening, the distal end of said tube having a blunt end to prevent the end of the catheter from traumatizing or becoming caught in the walls of a vessel into which the catheter is inserted, wherein said tube has a distal end portion extending from said second opening and terminating at said distal tip, and said planar axial divider extends to form a flat peripheral wall of said distal end portion, said flat peripheral wall exending to said blunt distal tip.

11. The double lumen catheter as claimed in claim 10, wherein the first opening in the distal end of said tube is eccentric with respect to the axis of the proximal cylindrical portion of the tube.

12. The double lumen catheter as claimed in claim 10, wherein the first and second lumens and said distal end portion each have a uniform "D" shaped cross section.

* * * * *

UNITED STATES PATENT AND TRADEMARK OFFICE
CERTIFICATE OF CORRECTION

PATENT NO. : 4,808,155

DATED : February 28, 1989

INVENTOR(S) : Sakharam D. Mahurkar

It is certified that error appears in the above-identified patent and that said Letters Patent is hereby corrected as shown below:

The title page should be deleted to appear as per attached title page.

Figures 1-6 should be deleted to be replaced with figures 1-6 as shown on the attached sheet.

Signed and Sealed this

Seventeenth Day of January, 1995

*Attest:*

BRUCE LEHMAN

*Attesting Officer*  *Commissioner of Patents and Trademarks*

United States Patent [19]

Mahurkar

[11] Patent Number: 4,808,155

[45] Date of Patent: Feb. 28, 1989

[54] SIMPLE DOUBLE LUMEN CATHETER

[76] Inventor: Sakharam D. Mahurkar, 6171 N. Sheridan Rd.-#1112, Chicago, Ill. 60660

[21] Appl. No.: 97,378

[22] Filed: Sep. 16, 1987

Related U.S. Application Data

[63] Continuation of Ser. No. 833,978, Feb. 27, 1986, abandoned, which is a continuation of Ser. No. 544,883, Oct. 24, 1983, abandoned.

[51] Int. Cl.$^4$ .............................................. A61M 25/00
[52] U.S. Cl. ............................................. 604/43; 604/4; 604/280
[58] Field of Search ................. 604/4, 5, 43-45, 604/280-284

[56] References Cited

U.S. PATENT DOCUMENTS

| | | | |
|---|---|---|---|
| D. 250,349 | 11/1978 | McFarlane | D24/54 |
| D. 254,444 | 3/1980 | Levine | D24/54 |
| 256,590 | 4/1882 | Pfarre | 604/43 |
| D. 256,617 | 8/1980 | Clemens | D24/54 |
| D. 272,651 | 2/1984 | Mahurkar | 604/44 X |
| 701,075 | 5/1902 | McCully | 604/43 |
| 998,339 | 7/1911 | Hollins | 27/24 A |
| 1,045,326 | 11/1912 | Ruflin | 604/43 |
| 1,093,538 | 4/1914 | Clough | 128/343 |
| 1,290,647 | 1/1919 | Nyvall | 128/214 R X |
| 1,922,084 | 8/1933 | Gerow | 128/349 |
| 2,175,726 | 10/1939 | Gebauer | 128/349 B |
| 2,230,218 | 2/1941 | Asche | 128/276 |
| 2,409,343 | 10/1946 | Curtis | 128/214 |
| 2,473,742 | 6/1949 | Auzin | 128/349 |
| 2,474,665 | 6/1949 | Guarino | 128/DIG. 3 |
| 2,564,977 | 8/1951 | Hsi Hu | 128/221 X |
| 2,590,895 | 4/1952 | Scarpellino | 128/221 |
| 2,625,932 | 1/1953 | Salisbury | 128/214.2 |
| 2,716,983 | 9/1955 | Windischman et al. | 128/221 |
| 2,819,718 | 1/1958 | Goldman | 128/350 |
| 2,930,378 | 3/1960 | Buyers | 128/354 |
| 3,042,045 | 7/1962 | Sheridan | 128/349 |
| 3,175,554 | 3/1965 | Stewart | 128/2 |
| 3,314,430 | 4/1967 | Alley et al. | 128/350 |
| 3,324,853 | 6/1967 | Czorny et al. | 128/214.4 |
| 3,331,371 | 7/1967 | Rocchi et al. | 128/349 |
| 3,359,974 | 12/1967 | Khalil | 128/2.05 |
| 3,394,705 | 7/1968 | Abramson | 128/349 |
| 3,435,826 | 1/1969 | Fogarty | 128/348 |
| 3,437,088 | 4/1969 | Bielinski | 128/2 |
| 3,448,739 | 6/1969 | Stark et al. | 128/2.0⊃ |
| 3,452,756 | 7/1969 | Harautuneian | 128/349 |
| 3,463,152 | 8/1969 | Sorenson | 128/214.4 |
| 3,467,101 | 9/1969 | Fogarty et al. | 128/348 |
| 3,543,758 | 12/1970 | McWhorter | 128/349 |
| 3,543,759 | 12/1970 | McWhorter | 128/349 |
| 3,550,591 | 12/1970 | MacGregor | 128/214.4 |
| 3,566,874 | 3/1971 | Sheperd et al. | 128/349 |
| 3,593,713 | 7/1971 | Bogoff et al. | 128/246 |
| 3,599,620 | 8/1971 | Balin | 128/349 B |
| 3,634,924 | 1/1972 | Blake et al. | 29/447 |
| 3,683,908 | 8/1972 | Michael et al. | 128/145.7 |
| 3,726,281 | 4/1973 | Norton et al. | 128/349 R |

(List continued on next page.)

FOREIGN PATENT DOCUMENTS 834211 2/1976 Belgium ................. 128/221

(List continued on next page.)

OTHER PUBLICATIONS

McIntosh et al., "Double Lumen Catheter," *J.A.M.A.*, Feb. 21, 1959, pp. 137/835–138/836.

(List continued on next page.)

*Primary Examiner*—Dalton L. Truluck
*Attorney, Agent, or Firm*—Stephen G. Rudisill

[57] ABSTRACT

A double lumen catheter having an elongated tube with a proximal cylindrical portion enclosing first and second lumens separated by an internal divider, the proximal end of the elongated tube connecting to two separate connecting tubes communicating with the respective first and second lumens for the injection and removal of blood, the first lumen extending from the proximal end of the elongated tube to a first opening at the distal end of the elongated tube, and the second lumen extending from the proximal end of the elongated tube to a second opening spaced a sufficient distance away from the first opening, in the longitudinal direction, to prevent mixing of the returned blood with the blood taken in, the tube having a non-conical and non-tapered distal end portion having a reduced cross-sectional area and extending from said second opening and terminating in a blunt end to prevent the end of the catheter from traumatizing or becoming caught in the walls of a blood vessel into which the catheter is inserted.

12 Claims, 1 Drawing Sheet

(12) EX PARTE REEXAMINATION CERTIFICATE (5688th)
United States Patent
Mahurkar (10) Number: US 4,808,155 C1
(45) Certificate Issued: Mar. 6, 2007

(54) SIMPLE DOUBLE LUMEN CATHETER

(76) Inventor: Sakharam D. Mahurkar, 6171 N. Sheridan Rd.-#1112, Chicago, IL (US) 60660

Reexamination Request:
No. 90/007,222, Sep. 24, 2004
No. 90/007,784, Oct. 27, 2005

Reexamination Certificate for:
Patent No.: 4,808,155
Issued: Feb. 28, 1989
Appl. No.: 07/097,378
Filed: Sep. 16, 1987

Certificate of Correction issued Jan. 17, 1995.

Related U.S. Application Data (63) Continuation of application No. 06/833,978, filed on Feb. 27, 1986, now abandoned, which is a continuation of application No. 06/544,883, filed on Oct. 24, 1983, now abandoned.

(51) Int. Cl.
*A61M 25/00* (2006.01)

(52) U.S. Cl. ............ 604/43; 604/523; 604/6.16
(58) Field of Classification Search ............ 604/6.16, 604/27–29, 43–45, 264, 523, 533–535, 537, 604/539
See application file for complete search history.

(56) References Cited

U.S. PATENT DOCUMENTS

| | | | |
|---|---|---|---|
| 1,852,427 A | 4/1932 | Lopatin |
| 4,134,402 A | 1/1979 | Mahurkar |
| 4,369,790 A | 1/1983 | McCarthy |
| 4,381,011 A | 4/1983 | Somers, 3rd |
| 4,403,984 A | 9/1983 | Ash et al. |
| 4,405,313 A | 9/1983 | Sisley et al. |
| 4,451,252 A | 5/1984 | Martin |
| 4,464,176 A | 8/1984 | Wijayarathna |
| 4,465,481 A | 8/1984 | Blake |
| 4,531,943 A | 7/1985 | Van Tassel et al. |
| 4,666,426 A | 5/1987 | Aigner |

FOREIGN PATENT DOCUMENTS

| | | |
|---|---|---|
| BE | 834211 | 2/1976 |
| CA | 50089 | 8/1982 |
| DE | 2814379 | 4/1978 |
| FR | 1285953 | 1/1962 |
| FR | 2297640 | 1/1975 |
| GB | 1503469 | 10/1976 |
| JP | 52-99543 | 8/1977 |

OTHER PUBLICATIONS

Excerpts of Trial Transcript, *Mahurkar* vs *VAS–CATH of Canada.*, vol. 4, Federal Court of Canada Trial Division; Nov. 27, 1987.
Per Odman, Percutaneous Selective Angiography of the Main Branches of the Aorta (Preliminary Report), Acta Radiologica, Jan. 1956, pp. 1–14, vol. 45.

(Continued)

*Primary Examiner*—David O. Reip (57) ABSTRACT

A double lumen catheter having an elongated tube with a proximal cylindrical portion enclosing first and second lumens separated by an internal divider, the proximal end of the elongated tube connecting to two separate connecting tubes communicating with the respective first and second lumens for the injection and removal of blood, the first lumen extending from the proximal end of the elongated tube to a first opening at the distal end of the elongated tube, and the second lumen extending from the proximal end of the elongated tube to a second opening spaced a sufficient distance away from the first opening, in the longitudinal direction, to prevent mixing of the returned blood with the blood taken in, the tube having a non-conical and non-tapered distal end portion having a reduced cross-sectional area and extending from said second opening and terminating in a blunt end to prevent the end of the catheter from traumatizing or becoming caught in the walls of a blood vessel into which the catheter is inserted.

OTHER PUBLICATIONS

Catalog, *Surgical Vinyl Specialty Catheters*, p. 5, "No. 1017 Cropp Exchange Transfusion Catheter", U.S. Catheter & Instrument Corporation, Glen Falls New York, 1968.

A. Cournand et al., Double Lumen Catheter for Intravenous and Intracardiac Blood Sampling and Pressure Recording, Proceedings of the Society for Experimental Biology and Medicine, Oct.–Dec. 1945, pp. 73–75, vol. 60, New York.

Catalog, The Cook Double Lumen Hemodialysis Catheter, Cook Incorporated, Bloomington Indiana, 1985.

Packing List No. 19108 and description of Hickman Dual Lumen Right Atrial Catheter, Evermed, Medina, Washington, May 25, 1982.

Tsuchiya et al., Design of a Two–Lumen Piercing Needle That is Capable of Carrying Out Dialysis by Single Puncture, Nippon Hinyokika Gakkaishi (Journal of the Urological Society of Japan), 1974, pp. 805–807, vol. 65 (12).

Decision, *Dr. Sakhaarm D. Mahurkar v. C.R. Bard, Inc., and Bard Access Systems, Inc.*, 95–1225, United States Court Of Appeal Fr The Federal Circuit, 79 F.3d 1572; 1996 U.S. App. Lexis 6078; 38 U.S.P.Q.2D (BNA) 1288, Mar. 29, 1996.

Decision, *Dr. Sakhaarm D. Mahurkar v. C.R. Bard, Inc., Bard Access Systems, Inc., and Bard Healthcare, Inc.*, No. 01 C 8452, United States District Court For The Northern District Of Illinois, Eastern Division, 2004 U.S. Dist. Lexis 18466, Sep. 7, 2004.

Bard's Prior Art Notice Under 35 U.S.C. § 282, *Dr. Sakharam D. Mahurkar v. C.R. Bard, Inc., d/b/a Davol*, U.S. District Court For the Northern District of Illinois, Eastern Division, Civil No. 92–C–4803, Jul. 8, 1994.

Prior Art Notice Under 35 U.S.C. § 282, *In The Matter Of Mahurkar Double Lumen Hemodialysis Catheter Patent Litigation*, U.S. District Court For the Northern District of Illinois, Eastern Division, No. MDL 853, Jul. 9, 1992.

Prior Art Notice Under 35 U.S.C. § 282, *In The Matter Of Mahurkar Double Lumen Hemodialysis Catheter Patent Litigation*, U.S. District Court For the Northern District of Illinois, Eastern Division, No. MDL 853, Jul. 10, 1992.

Dr. Mahurkar's Proposed Memorandum Order Denying Bard's Motion for Judgment As A Matter of Law And For New Trial, *Dr. Sakharam D. Mahurkar v. C.R. Bard, Inc., d/b/a Davol*, U.S. District Court For the Northern District of Illinois, Eastern Division, Civil No. 92–C–4803.

Bard's Responses to Mahurkar's First Request For Admissions, *Dr. Sakharm D. Mahurkar v. C.R. Bard, Inc., d/b/a/ Davol*, U.S. District Court For the Northern District of Illinois, Eastern Division, Civil No. 92–C–4803, Jul. 6, 1993.

Dr. Mahurkar's Supplemental Responses To Bard's Interrogation Nos. 2 and 8 (B), *Dr. Sakharam D. Mahurkar v. C.R. Bard, Inc., d/b/a Davol*, U.S. District Court For the Northern District of Illinois, Eastern Division, Civil No. 92–C–4803, Nov. 5, 1992.

Bard's Reply Memorandum in Support Of Its Renewed Motion For Judgment As A Matter Of Law Of Noninfringement and Invalidity Due To Obviousness, *Dr. Sakharm D. Mahurkar v. C.R. Bard, Inc., d/b/a Davol*, U.S. District Court For the Northern District of Illinois, Eastern Division, Civil No. 92–C–4803, Nov. 9, 1994.

Bard's Motion For Entry Of Judgment As A Matter Of Law Of Invalidity Of The '155 Patent On The Grounds Of Printed Publication And On–Sale Bars Under 35 U.S.C. § 102(b) And For Obviousness Under 35 U.S.C. § 103, *Dr. Sakharam D. Mahurkar v. C.R. Bard, Inc., d/b/a Davol*, U.S. District Court For the Northern District of Illinois, Eastern Division, Civil No. 92–C–4803, Aug. 25, 1994.

Second Supplemental Answers To Interrogatories By C. R. Bard, Inc., Davol Inc. And Bard Access Systems, Inc., *Dr. Sakharam D. Mahurkar v. C.R. Bard, Inc., d/b/a Davol*, U.S. District Court For the Northern District of Illinois, Eastern Division, Civil No. 92–C–4803, Jan. 8, 1993.

Declaration of Stephen R. Ash, *Dr. Sakharam D. Mahurkar v. C.R. Bard, Inc. d/b/a Davol*, U.S. District Court For the Northern District of Illinois, Eastern Division, Civil No. 92–C–4803, May 20, 1993.

Declaration of Stephen R. Ash, *Dr. Sakharam D. Mahurkar v. C.R. Bard, Inc., d/b/a Davol*, U.S. District Court For the Northern District of Illinois, Eastern Division, Civil No. 92–C–4803,, May 26, 1994.

Declaration of Sakharam D. Mahurkar, *Dr. Sakharam D. Mahurkar v. C.R. Bard, Inc., d/b/a Davol*, U.S. District Court For the Northern District of Illinois, Eastern Division, Civil No. 92–C–4803,, May 20, 1993.

Rebuttal Expert Report of Sakharam D. Mahurkar, *Dr. Sakharam D. Mahurkar v. C.R. Bard Access Systems, Inc. and Bard Healthcare, Inc.*, U.S. District Court For the Northern District of Illinois, Eastern Division, Civil No. 01–C–8452,, Feb. 4, 2004.

Rebuttal Expert Report of Ronald Luther, *Dr. Sakharam D. Mahurkar v. C.R. Bard Access Systems, Inc., and Bard Healthcare, Inc.*, U.S. District Court For the Northern District of Illinois, Eastern Division, Civil No. 01–C–8452,, Jan. 9, 2004.

Expert Report of Dr. Thomas Kinney Regarding Invalidity Of U.S. Patent No. 4,808,155, *Dr. Sakharam D. Mahurkar v. C.R. Bard Access Systems, Inc., and Bard Healthcare, Inc.*, U.S. District Court For the Northern District of Illinois, Eastern Division, Civil No. 01–C–8452,, Jan. 7, 2004.

Consent Judgment Order, *In The Mater of Mahurkar Double Lumen Hemodialysis Patent Litigation*, U.S. District Court for The Northern District of Illinois, Eastern Division, No. MDL 853 90–CV–05909, Apr. 30, 1992.

Examination Before Trial Of USCI, Inc. In The Matter of Mahurkar Double Lumen Hemodialysis Catheter Patent Litigation, U.S. District Court for The Northern District of Illinois, Eastern Division, No. MDL 853, Jun. 29, 1992 at 19–20.

Chronological Index of Mahurkar Documents and attachments, relating to the conception and reduction to practice of the invention of U.S. Patent 4,808,155.

Dr. Mahurkar Supplemental Exhibits Nos. 1–22, relating to the conception and reduction to practice of the invention of U.S. Patent 4,808,155.

P. Dittrich et al., "Hämodialyse und Peritonealdialyse", Springer Verlag, Berlin, Heidelberg, New York 1969, Library of Congress Catalog Card No. 68–24618, pp. 118–120 (German text and English translation).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 is confirmed.

* * * * *